United States Patent
Zeidler et al.

[19]

[11] Patent Number: 6,001,391
[45] Date of Patent: Dec. 14, 1999

[54] PROCESS FOR PRODUCING SOLID DRUG FORMS HAVING AT LEAST TWO PHASES

[75] Inventors: Jürgen Zeidler, Mutterstadt; Joerg Rosenberg, Ellerstadt; Jörg Breitenbach, Mannheim; Andreas Kleinke, Ludwigshafen; Werner Maier, Schifferstadt, all of Germany

[73] Assignee: Basf Aktiengesellschaft, Ludwigshafen, Germany

[21] Appl. No.: 09/037,706

[22] Filed: Mar. 10, 1998

[30] Foreign Application Priority Data

Mar. 12, 1997 [DE] Germany .................. 197 10 213

[51] Int. Cl.⁶ .............. A61K 9/20; A61K 9/24; A61K 9/44; A61J 3/10
[52] U.S. Cl. .......... 424/467; 424/472; 424/464; 424/468; 424/465; 424/480; 424/482
[58] Field of Search .............. 424/464, 472, 424/467, 468, 465, 480, 482

[56] References Cited

U.S. PATENT DOCUMENTS

| | | | |
|---|---|---|---|
| 4,801,460 | 1/1989 | Goertz et al. | 424/465 |
| 4,880,585 | 11/1989 | Klimesch et al. | 264/141 |
| 4,957,681 | 9/1990 | Klimesch et al. | 264/211 |
| 5,073,379 | 12/1991 | Klimesch et al. | 424/467 |
| 5,552,159 | 9/1996 | Mueller et al. | |

FOREIGN PATENT DOCUMENTS

| | | |
|---|---|---|
| 0 358 107 | 3/1990 | European Pat. Off. . |
| 2073278 | 10/1971 | France . |
| 4446468 | 12/1994 | Germany . |
| 97/15293 | 5/1997 | WIPO . |

*Primary Examiner*—Thurman K. Page
*Assistant Examiner*—Brian K. Seidleck
*Attorney, Agent, or Firm*—Keil & Weinkauf

[57] ABSTRACT

A process for producing solid combination tablets which have at least two phases comprises molding a melt of a polymeric binder with or without at least one active ingredient, there being at least one solid product, which may contain an active ingredient incorporated into the still plastic composition during the molding step.

16 Claims, 1 Drawing Sheet

PROCESS FOR PRODUCING SOLID DRUG FORMS HAVING AT LEAST TWO PHASES

DESCRIPTION

The present invention relates to a process for producing solid combination drug forms which have at least two phases and are based on at least one pharmacologically acceptable polymeric binder and at least one pharmaceutical active ingredient, and to the combination drug forms obtainable thereby.

Classical processes for producing solid drug forms, especially tablets, are carried out batchwise and comprise a plurality of stages. The starting material generally used therein comprises pharmaceutical granules. The production both of the granules and of the solid drug forms is time-consuming and costly. This is particularly true when combination products are to be produced in order to include different active ingredients in one drug form or in order to achieve different release characteristics.

A considerably simpler continuous process for producing solid drug forms has been known for some time and entails extruding a solvent-free melt of a polymeric binder containing active ingredients, and shaping this extrudate to the required drug form, for example in a calender with molding rolls, see EP-A-240 904, EP-A-240 906, EP-A-337 256 and EP-A-358 105. However, this process does not permit the combination of two mutually incompatible active ingredients in one drug form or the accomplishment of different release characteristics.

DE-A-44 46 468.4 describes the production of covered tablets from a polymer melt containing active ingredients using a calender with molding rolls, where the polymer melt containing active ingredients is introduced between two sheets of the covering material into the molding rolls. It is true that this process thus makes it possible to provide another active ingredient in the sheets and to provide the tablets with, for example, an enteric coating. However, there are narrow limits on the nature and amount of the active ingredients in the sheets so that the tablets produced in this way are not universally applicable.

DE 195 39 361.9 (which is not a prior publication) describes the coextrusion of at least two polymer melts, at least one of which contains an active ingredient, to result in tablets consisting of at least two sequential layers or of at least two coaxial layers (core/shell), depending on the coextrusion die.

It is an object of the present invention to provide a process for producing solid combination drug forms which is straightforwardly and generally applicable and makes it possible to produce a wide variety of such combination drug forms.

We have found that this object is achieved in the molding of a drug form from a melt of a polymeric binder when at least one solid product is taken up in the still plastic composition, the melt and/or the product containing at least one active ingredient.

The present invention therefore relates to a process for producing solid combination drug forms which have at least two phases and are based on at least one pharmacologically acceptable polymeric binder and at least one pharmaceutical active ingredient, which comprises molding a melt of the polymeric binder (binder A) with or without at least one active ingredient, and incorporating in the still plastic composition during the molding step at least one solid product which may contain at least one active ingredient.

To produce the melt it is necessary to mix the ingredients, namely at least one pharmacologically acceptable polymeric binder (binder A), with or without at least one pharmaceutical active ingredient and with or without conventional additives, and to melt them to a plastic mixture, preferably in the absence of a solvent. The process steps can be carried out in a known manner, for example as described in EP-A-240 904, EP-A-337 256 and EP-A-358 105. The contents of these publications are incorporated herein by reference.

The components can be firstly mixed and then melted and homogenized. However, it has proven preferable, especially on use of sensitive active ingredients, first to melt the polymeric binder and mix it where appropriate with conventional pharmaceutical additives, operating the apparatus such as stirred vessels, stirrers, solids mixers etc. where appropriate alternately, and then to mix in (homogenize) the sensitive active ingredient(s) in the plastic phase with very small residence times in intensive mixers. The active ingredient(s) can be employed in solid form or as solution or dispersion.

The melting and mixing take place in an apparatus customary for these purposes. Particularly suitable are extruders or heatable containers with stirrers, eg. kneaders (such as of the type mentioned below).

Mixing apparatus which can be used is also that employed for mixing in plastics technology. Suitable types of apparatus are described, for example, in "Mischen beim Herstellen und Verarbeiten von Kunststoffen", H. Pahl, VDI-Verlag, 1986. Particularly suitable mixing apparatus comprises extruders and dynamic and static mixers, and stirred vessels, single-shaft stirrers with stripper mechanisms, especially paste mixers, multishaft stirrers, especially PDSM mixers, solids mixers and, preferably, mixer/kneader reactors (eg. ORP, CRP, AP, DTB supplied by List or Reactotherm supplied by Krauss-Maffei or Ko-Kneter supplied by Buss), trough mixers and internal mixers or rotor/stator systems (eg. Dispax supplied by IKA).

In the case of sensitive active ingredients it is preferable first for the polymeric binder to be melted in an extruder and then for the active ingredient to be admixed in a mixer/kneader reactor. On the other hand, with less sensitive active ingredients, a rotor/stator system can be employed for vigorously dispersing the active ingredient.

The mixing apparatus is charged continuously or batchwise, depending on its design, in a conventional way. Powdered components can be introduced in a free feed, eg. via a way feeder. Plastic compositions can be fed in directly from an extruder or via a gear pump, which is particularly advantageous if the viscosities and pressures are high. Liquid media can be metered in by a suitable pump unit.

The mixture obtained by mixing and melting the binder with or without the active ingredient and with or without the additive(s) ranges from pasty to viscous (plastic) and is thus extrudable. The binder should preferably be soluble or swellable in a physiological medium. Examples of suitable binders are:

Polyvinylpyrrolidone (PVP), copolymers of N-vinylpyrrolidone (NVP) and vinyl esters, especially vinyl acetate, copolymers of vinyl acetate and crotonic acid, partially hydrolyzed polyvinyl acetate, polyvinyl alcohol, poly(hydroxyalkyl acrylates), poly(hydroxyalkyl methacrylates), polyacrylates and polymethacrylates (Eudragit types), copolymers of methyl methacrylate and acrylic acid, cellulose esters, cellulose ethers, especially methylcellulose and ethylcellulose, hydroxyalkylcelluloses, especially hydroxypropylcellulose, hydroxyalkylalkylcelluloses, especially hydroxypropylethylcellulose, cellulose phthalates, especially cellulose acetate phthalate and hydroxypropylmethylcellulose phthalate, and mannans, especially galactomannans. The K values (according to H. Fikentscher, Cellulose-Chemie 13 (1932) 58–64 and 71–74) of the polymers are in the range from 10 to 100, preferably 12 to 70, in particular 12 to 35, and for PVP>17, in particular 20 to 35.

It is also possible to use biodegradable polymers such as polyhydroxyalkanoates, eg. polyhydroxybutyric acid, polylactic acid, polyamino acids, eg. polylysine, polyasparagine, polydioxans and polypeptides.

Preferred polymeric binders are polyvinylpyrrolidone, copolymers of N-vinylpyrrolidone and vinyl esters, poly (hydroxyalkyl acrylates), poly(hydroxyalkyl methacrylates), polyacrylates, polymethacrylates, alkylcelluloses and hydroxyalkylcelluloses.

The polymeric binder must soften or melt in the complete mixture of all the components in the range from 50 to 180° C., preferably 60 to 130° C. The glass transition temperature of the mixture must therefore be below 180° C., preferably below 130° C. It is reduced if necessary by conventional pharmacologically acceptable plasticizing auxiliaries. The amount of plasticizer does not exceed 30% of the total weight of binder and plasticizer in order to produce storage-stable drug forms which show no cold flow. However, the mixture preferably contains no plasticizer.

Examples of such plasticizers are:

long-chain alcohols, ethylene glycol, propylene glycol, glycerol, trimethylolpropane, triethylene glycol, butanediols, pentanols such as pentaerythritol, hexanols, polyethylene glycols, polypropylene glycols, polyethylene/propylene glycols, silicones, aromatic carboxylic esters (eg. dialkyl phthalates, trimellitic esters, benzoic esters, terephthalic esters) or aliphatic dicarboxylic esters (eg. dialkyl adipates, sebacic esters, azelaic esters, citric and tartaric esters), fatty acid esters such as glycerol mono-, di- or triacetate or sodium diethyl sulfosuccinate. The plasticizer concentration is generally from 0.5 to 15, preferably 0.5 to 5, % of the total weight of the mixture.

Conventional pharmaceutical auxiliaries, the total amount of which can be up to 100% of the weight of the polymer, are for example: extenders or bulking agents such as silicates or diatomaceous earth, magnesium oxide, alumina, titanium oxide, methylcellulose, sodium carboxymethylcellulose, talc, sucrose, lactose, cereal or corn starch, potato flour, polyvinyl alcohol, especially in a concentration of from 0.02 to 50, preferably 0.20 to 20, % of the total weight of the mixture;

lubricants and release agents such as magnesium, aluminum and calcium stearate, talc and silicones, and animal or vegetable fats, especially in hydrogenated form and those which are solid at room temperature. These fats preferably have a melting point of 50° C. or above. Triglycerides of $C_{12}$, $C_{14}$, $C_{16}$ and $C_{18}$ fatty acids are preferred. It is also possible to use waxes such as carnauba wax. These fats and waxes can advantageously be admixed alone or together with mono- and/or diglycerides or phosphatides, especially lecithin. The mono- and diglycerides are preferably derived from the abovementioned types of fatty acids. The total amount of lubricants and release agents is preferably 0.1 to 5% of the total weight of the composition for each layer;

flow regulators, eg. Aerosil, in an amount of from 0.1 to 5% of the total weight of the mixture;

dyes, such as azo dyes, organic or inorganic pigments or dyes of natural origin, with inorganic pigments in a concentration of from 0.001 to 10, preferably 0.5 to 3, % of the total weight of the mixture being preferred;

stabilizers such as antioxidants, light stabilizers, hydroperoxide destroyers, radical scavengers, stabilizers against microbial attack.

It is also possible to add wetting agents, preservatives, disintegrants, adsorbents, mold release agents and propellants (cf., for example, H. Sucker et al. Pharmazeutische Technologie, Thieme-Verlag, Stuttgart 1978).

Auxiliaries also mean for the purpose of the invention substances for producing a solid solution containing the pharmaceutical active ingredient. Examples of these auxiliaries are pentaerythritol and pentaerythritol tetraacetate, polymers such as polyethylene oxides and polypropylene oxides and their block copolymers (poloxamers), phosphatides such as lecithin, homo- and copolymers of vinylpyrrolidone, surfactants such as polyoxyethylene 40 stearate, and citric and succinic acids, bile acids, sterols and others as indicated, for example, by J. L. Ford, Pharm. Acta Helv. 61 (1986) 69–88.

Pharmaceutical auxiliaries are also regarded as being bases and acids added to control the solubility of an active ingredient (see, for example, K. Thoma et al., Pharm. Ind. 51 (1989) 98–101).

The only precondition for the suitability of auxiliaries is a sufficient thermal stability.

The extrusion of the plastic mixture likewise takes place in a conventional way. The extrusion preferably takes place with the aid of a calender with two molding rolls which make contact along a surface line and rotate in opposite directions. The molding rolls have on their surface depressions which correspond to the shape of one half of the required drug form. The drug form is shaped in the area of contact of the two rolls by combining the tablet composition in one depression on one roll with that in the opposite depression on the other roll.

The shape of the depressions and thus of the drug form can be chosen substantially as desired. Particularly expedient depressions have elongate and ellipsoidal segments so that oblong tablets or lenticular tablets are obtained. It is moreover possible for the depressions on one molding roll to be different from the depressions on the other molding roll. In addition, one molding roll with depressions may be combined with a smooth roll. It has furthermore proven expedient in some cases to cover the depressions with a mold release agent in order to facilitate detachment of the drug form from the molding rolls. Examples of suitable mold release agents are silicone resins, stearic acid, calcium or magnesium stearate, paraffin, cetyl alcohol or lecithins.

The molding rolls can be heatable or coolable, and it is preferred to cool at least the molding roll into whose depressions the melt of binder (B) containing active ingredient is introduced (see below).

The melt is fed to the molding rolls in a conventional way, but preferably as extruded strand or extruded ribbon.

During the extrusion, at least one solid product which may contain at least one active ingredient is taken up in the still plastic composition. If the melt of the polymeric binder contains an active ingredient, it may be the same or a different active ingredient. This results (after cooling) in a solid combination drug form consisting of at least two phases, the first phase comprising the polymeric binder (A) with or without at least one pharmaceutical active ingredient and with or without pharmaceutical additives. The second phase formed by the solid product can be incorporated into the first phase in such a way that part of its surface remains visible (ie. the drug form does not have a core/sheath structure). However, it can also be completely taken up in the first phase.

A suitable solid product is any solid drug form provided it does not "fuse" homogeneously with the first phase but is able to form its own phase. Examples of suitable solid products are tablets, a solidified melt of a pharmacologically acceptable polymeric binder (binder B) containing active ingredient, a solidified active ingredient melt, pills, pellets or active ingredient crystals, which contain the active ingredient in a conventional carrier such as alkylcelluloses, for example methyl- or ethylcellulose, hydroxyalkylcelluloses, for example hydroxyethyl-or hydroxypropylcellulose, starch, lactic acid, sugars such as lactose, sorbitol, isomalt, calcium hydrogen phosphate etc. The solid product can be uncoated or coated in a conventional way, eg. with the film coatings mentioned hereinafter.

Conventional tablets or film-coated tablets are preferably used as solid product.

It is particularly preferred for the melt of polymeric binder (B) containing active ingredient or the active ingredient melt to be allowed to solidify in the depressions of a molding roll. For this purpose, the melt is introduced in the required amount and in low-viscosity form into the depressions of at least one molding roll. It is allowed to solidify there, for example by blowing cooled air onto the molding roll or by cooling it. The parts of the solidified melt are then taken up, during the extrusion, into the still plastic melt of the polymeric binder (A) containing active ingredient.

Pharmaceutical active ingredients mean for the purpose of the invention all substances with a pharmaceutical action and minimal side effects as long as they undergo negligible decomposition under the processing conditions. The amount of active ingredient per dose unit and the concentration may vary within wide limits depending on the activity and the rate of release. The only condition is that they suffice to achieve the required effect. Thus, the concentration of active ingredient can be in the range from 0.001 to 95, preferably from 20 to 80, in particular 30 to 70, % by weight. It is also possible to employ combinations of active ingredients. Active ingredients for the purpose of the invention are also vitamins and minerals, as well as crop treatment agents and insecticides. The vitamins include the vitamins of the A group, of the B group, meaning not only $B_1$, $B_2$, $B_6$ and $B_{12}$ plus nicotinic acid and nicotinamide but also compounds with vitamin B properties such as adenine, choline, pantothenic acid, biotin, adenylic acid, folic acid, orotic acid, pangamic acid, carnitine, p-aminobenzoic acid, myoinositol and lipoic acid, and vitamin C, vitamins of the D group, E group, F group, H group, I and J group, K group and P group. Active ingredients for the purpose of the invention also include therapeutic peptides and vaccines.

The process according to the invention is suitable, for example, for processing the following active ingredients and the pharmacologically active salts thereof:

acebutolol, acetylcysteine, acetylsalicylic acid, acyclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazolin, cefixime, cefotaxime, ceftazidime, ceftriaxone, cefuroxim, selegiline, chloramphenicol, chlorhexidine, chlor-pheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphen, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavine mononucleotide, fluconazole, flunarizine, fluorouracil, fluoxetine, flurbiprofen, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures and combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, pentoxifylline, phenoxymethylpenicillin, phenylephrine, phenylpropanolamine, phenytoin, piroxicam, polymyxin B. povidone iodine, pravastatin, prazepam, prazosin, prednisolone, prednisone, bromocriptine, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproic acid, vancomycin, verapamil, vitamin E, folinic acid, zidovudine.

Preferred active ingredients are ibuprofen (as racemate, enantiomer or enriched enantiomer), ketoprofen, flurbiprofen, acetylsalicylic acid, verapamil, paracetamol, nifedipine, captopril, omeprazole, ranitidine, tramadol, cyclosporin, trandolapril and therapeutic peptides.

In specific cases there may be formation of solid solutions. The term "solid solutions" is familiar to the skilled worker, for example from the literature cited at the outset. In solid solutions of pharmaceutical active ingredients in polymers, the active ingredient is present in the form of a molecular dispersion in the polymer.

Solid combination drug forms which have at least two phases and can be prepared by the process according to the invention are, in particular, tablets, preferably oblong tablets, coated tablets, pastilles and pellets. The resulting drug forms can also finally be provided in a conventional way with film coatings which control the release of active ingredient or mask the taste.

Suitable materials for such coatings are polyacrylates such as the Eudragit types, cellulose esters, such as hydroxypropylmethylcellulose phthalates, and cellulose ethers such as ethylcellulose, hydroxypropylmethylcellulose or hydroxypropylcellulose.

The process according to the invention makes it possible to produce combination drug forms which may contain one or more active ingredients, in particular either in the solidified melt of the binder (A) or in the solid product or in both. It is moreover possible to vary the release characteristics of the active ingredient(s) in the required manner by the choice of appropriate binders. It is additionally possible to combine incompatible active ingredients together. For example, it is possible to produce sustained release (SR) tablets with an instant release (IR) content. These advantageously have a structure such that the solid product forms the IR content. Particularly suitable binders for this purpose are polyvinylpyrrolidones and copolymers of N-vinylpyrrolidone and vinyl acetate, and sugars such as lactose, sorbitol or isomalt. The sustained release content contains the abovementioned cellulose derivatives in particular as binders. It is additionally possible to produce SR/SR or IR/IR combinations. Corresponding considerations apply to combination drug forms with two or more different active ingredients.

BRIEF DESCRIPTION OF THE DRAWINGS

The following Examples illustrate the invention without restricting it.

The production of a combination drug form according to the invention is illustrated in detail below by means of FIGS. 1 and 2, where.

Figure 1:
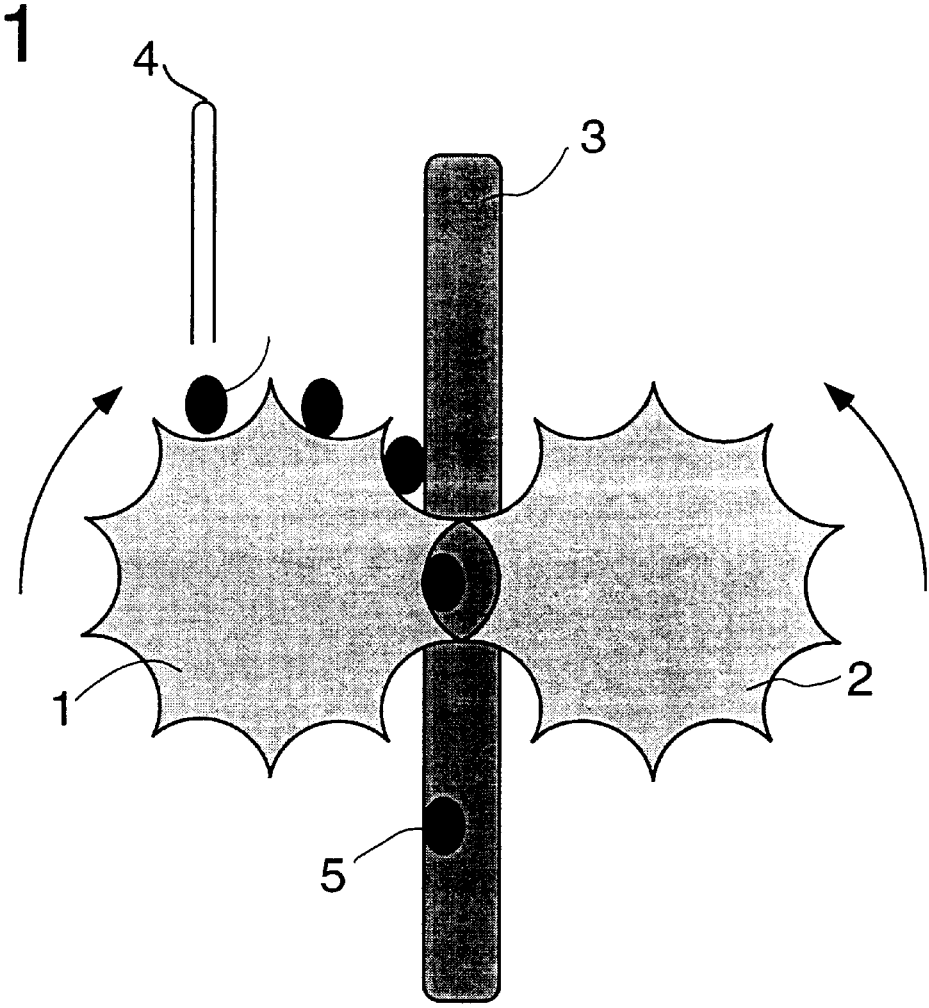
FIG. 1 shows a diagrammatic representation of the production process using two molding rolls

The extrusion process with the aid of two molding rolls 1, 2 is illustrated diagrammatically in FIG. 1. Molding rolls 1, 2 rotate in opposition directions, the direction of rotation being indicated by the arrows. A strand 3 coming from an extruder and consisting of a polymeric binder containing active ingredient is introduced in the direction of the arrow between the two molding rolls 1, 2. The strand 3 is in the plastic state. At the same time, the required amount of a melt of a polymeric binder (B) containing active ingredient is introduced from a metering station 4 into the depressions in molding roll 1. Molding roll 1 is cooled so that the plastic melt solidifies immediately. Rotation of molding rolls 1, 2 in opposite directions results in tablets 7 being punched out of the strand 3, with the solidified melt 5 present in the relevant depression being incorporated into each tablet. If necessary, the tablets are subsequently cooled and, if required, provided with a film coating.

EXAMPLE 1

Production of a sustained release tablet with an instant release content:

Klucel EF (hydroxypropylcellulose), Methocel K4M (methylcellulose and methylcellulose derivatives which simultaneously contain ethyl, hydroxyethyl, hydroxypropyl or carboxymethyl ether groups), lecithin and verapamil hydrochloride are mixed and melted in an extruder in amounts such that the resulting melt has the following composition:

| Verapamil hydrochloride | 48% |
|---|---|
| Klucel EF | 31.5% |
| Methocel K4M | 17.5% |
| Lecithin | 3% |

Mixing, melting and extrusion take place in an extruder under the following conditions:

| | Section 1 | Section 2 | Section 3 | Section 4 | Head |
|---|---|---|---|---|---|
| Temp. | 80° C. | 100° C. | 110° C. | 110° C. | 115° C. |

For the IR content, verapamil hydrochloride is dissolved or dispersed in isomalt or Kollidon (polyvinylpyrrolidone) or a mixture thereof.

Figure 2:
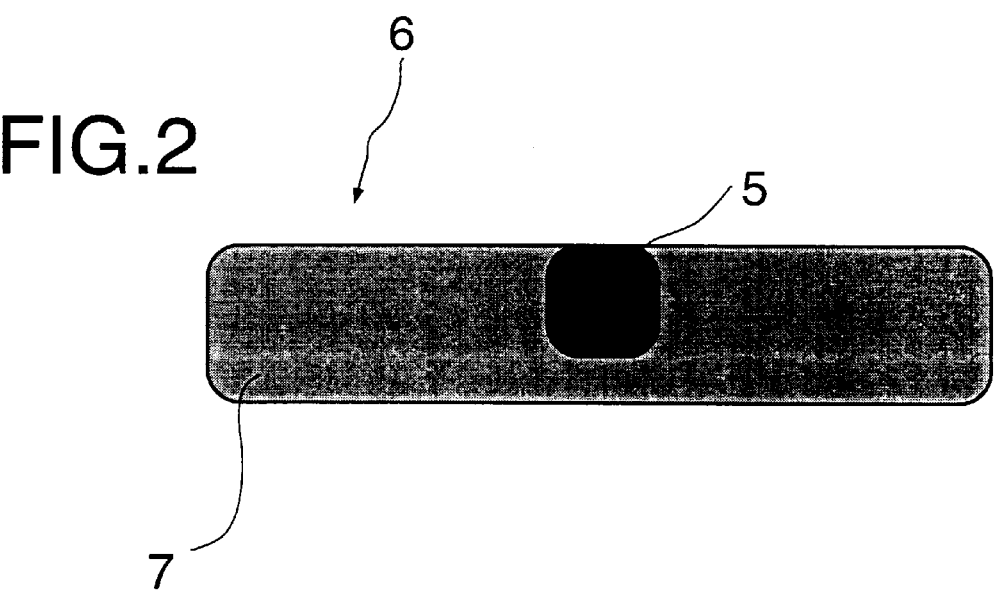
FIG. 2 shows a longitudinal section through a combination tablet according to the invention obtained by the method shown in FIG. 1.

This solution or dispersion is introduced from a metering station in an amount of 50 mg into the depressions of a molding roll, cf. the above description of the Figures. At the same time, the strand emerging from the extruder for the SR content is extruded with the aid of the molding rolls as described above to give oblong tablets of the type shown in FIG. 2.

EXAMPLE 2

The process indicated in Example 1 is repeated but using as IR content a conventional IR tablet of the following composition:

| Verapamil HCl | 40% |
|---|---|
| Ludipress[1)] | 59% |
| Magnesium stearate | 1% |
| 1) Lactose monohydrate | 43% |
| Kollidon CC | 3.5% |
| Kollidon 30 | 3.5% |

A corresponding tablet is obtained on use of pellets of the following composition as IR content:

| Paracetamol | 72% |
|---|---|
| Isomalt | 17.25% |
| Kollidon K30 | 4% |
| SDS | 0.75% |
| (sodium lauryl sulfate) | |
| Prinojel | 5% |
| (sodium carboxymethyl starch) | |
| Hydrogenated castor oil 259/hz/bw | 1% |

We claim:

1. A process for producing solid combination drug forms which have at least a first phase and a second phase, wherein at least the first phase contains a pharmacologically acceptable polymeric binder and at least one of the first and the second phase contains a pharmaceutically active ingredient, comprising (i) providing a plastic melt of a polymeric binder (binder A) with or without at least one active ingredient, which forms the first phase, (ii) molding the plastic melt to the drug form, and (iii) incorporating in the plastic melt during the molding step at least one solid product which may contain at least one active ingredient which solid product forms the second phase.

2. The process of claim 1, wherein the solid product is a solidified melt of a pharmacologically acceptable polymeric binder (binder B) containing an element of the group consisting of active ingredient, a solidified active ingredient, a solidified active ingredient melt, a tablet, a pill, a pellet, active ingredient crystals and mixtures thereof.

3. The Process of claim 2, wherein binder (B) is selected from the group consisting of an alkylcellulose, hydroxyalkylcellulose, carboxyalkylcellulose, polyvinylpyrrolidone, a copolymer of N-vinylpyrrolidone and vinyl acetate, a sugar alcohol and a polyethylene glycol.

4. The process of claim 1, wherein the molding of the melt takes place by extruding and shaping in a calender with molding rolls which rotate in opposite directions and have on their surface depressions to receive and shape the melt.

5. A process as claimed in claim 4, wherein the solid product is introduced into the depressions of one molding roll.

6. A process as claimed in claim 5, wherein the melt of polymeric binder (B) containing active ingredient or the active ingredient melt is introduced into the depressions of one molding roll, and the melt is caused to solidify.

7. A process as claimed in claim 4, wherein two molding rolls which have different depressions are combined.

8. A process as claimed in claim 4, wherein a molding roll with depressions is combined with a smooth roll.

9. A process as claimed in claim 4, wherein the depressions of the molding roll(s) are coated with a mold release agent.

10. A process as claimed in claim 1, wherein the combination drug forms are provided with a coating.

11. A solid combination drug form which has at least two phases which comprises a first phase of at least one pharmacologically acceptable polymeric binder (binder A) in the form of a solidified melt optionally containing, at least one pharmaceutically active ingredient and into which a solid product which contains at least one active ingredient is taken up as second phase.

12. A combination drug form as defined in claim 11, wherein the solid product is a solidified melt of a pharmacologically acceptable polymeric binder (binder B) containing one or more of an element selected from the group consisting of active ingredient, a solidified active ingredient melt, a tablet, a pill, a pellet, active ingredient crystals.

13. A combination drug form as defined in claim 12, wherein the binder (B) is an alkylcellulose, hydroxyalkylcellulose, carboxyalkylcellulose, polyvinylpyrrolidone, a copolymer of N-vinylpyrrolidone and vinyl acetate, a sugar alcohol or a polyethylene glycol.

14. A combination drug form as defined in claim 11 in the form of a tablet.

15. A combination drug form as defined in claim 11, which is provided with a coating.

16. A solid combination drug form which has at least two phases and is obtained by a process as defined in claim 1.

* * * * *

UNITED STATES PATENT AND TRADEMARK OFFICE
CERTIFICATE OF CORRECTION

PATENT NO.: 6,001,391

DATED: December 14, 1999

INVENTOR(S): ZEIDLER et al.

It is certified that error appears in the above-identified patent and that said Letters Patent is hereby corrected as shown below:

Col. 9, claim 3, line 19, "The Process" should be --The process--.

Col. 9, claim 5, line 28, "A process as claimed in" should be --The process of--.

Col. 9, claim 6, line 31, "A process as claimed in" should be --The process of--.

Col. 10, claim 7, line 1, "A process as claimed in" should be --The process of--.

Col. 10, claim 8, line 3, "A process as claimed in" should be --The process of--.

Col. 10, claim 9, line 5, "A process as claimed in" should be --The process of--.

Col. 10, claim 10, line 8, "A process as claimed in" should be --The process of--.

Col. 10, claim 11, line 13, delete the comma after "containing".

Signed and Sealed this

Eleventh Day of July, 2000

Attest:

Q. TODD DICKINSON

*Attesting Officer*        *Director of Patents and Trademarks*